United States Patent [19]

Thomas et al.

[11] Patent Number: 5,210,339

[45] Date of Patent: May 11, 1993

[54] PROCESS FOR NITRATING BENZOCYCLOBUTENE COMPOUNDS

[75] Inventors: P. J. Thomas; R. Garth Pews, both of Midland, Mich.

[73] Assignee: The Dow Chemical Company, Midland, Mich.

[21] Appl. No.: 868,812

[22] Filed: Apr. 15, 1992

[51] Int. Cl.$^5$ .................. C07C 205/06; C07C 205/12
[52] U.S. Cl. ...................... 568/929; 568/932; 568/934; 568/939; 568/940
[58] Field of Search .............. 568/939, 940, 929, 932, 568/937

[56] References Cited

U.S. PATENT DOCUMENTS

| | | | |
|---|---|---|---|
| 3,466,330 | 9/1969 | Tanida et al. | 260/578 |
| 4,216,188 | 8/1980 | Shabrua et al. | 423/118 |
| 4,248,739 | 2/1981 | Vaughan et al. | 252/455 |
| 4,540,763 | 9/1985 | Kirchhoff | 526/281 |
| 4,711,964 | 12/1987 | Tan et al. | 548/461 |

OTHER PUBLICATIONS

*Tetrahedron*, vol. 20 (1964), pp. 2185-2194, Lloyd et al., The Electrophilic Substitution of Benzocyclobutene-1.
*Chem. lett.*, (1988), pp. 1839-1842, Cornelis et al.; Regioselective Liquid-Phase Toluene Nitration with Modified Clays as Catalysts.
*Tetrahedron Lett.*, vol. 29, (1988), pp. 5905-5912, Cornelis et al.; A Procedure for Quantative Regioselective Nitration of Aromatic Hydrocarbons in the Laboratory.
*J. Org. Chem.*, vol. 52 (1987), pp. 2407-2410, Laszlo et al., Vastly Improved Para Preference in the Nitration of Halobenzenes.
*J. Org. Chem.*, vol. 43, No. 14(1978), pp. 2923-2925, Still et al.; Rapid Chromatographic Technique for Preparative Separations with Moderate Resolution.
*Advanced Materials in Catalysis*, (1977), pp. 209-233, H. E. Swift; Catalytic Properties of Synthetic Layered Silicates and Aluminosilicates.

Primary Examiner—Marianne M. Cintins
Assistant Examiner—John Peabody
Attorney, Agent, or Firm—Charlotte M. Kraebel; Charles J. Enright

[57] ABSTRACT

An improved process for the nitration of a substituted or unsubstituted benzocyclobutene compound in a reaction mixture comprising a nitrating agent, an unhalogenated carboxylic acid anhydride, clay and a solvent to produce a corresponding nitrobenzocyclobutene compound, is that wherein:

(a) the solvent has a density above that of the nitrating agent or an extractable precursor thereof;
(b) the reaction mixture is heated at a temperature such that solvent is removed from the reaction mixture to a site outside the reaction mixture to extract nitrating agent or extractable precursor thereof; and
(c) the thus-extracted nitrating agent or precursor thereof is fed into the reaction mixture to nitrate the benzocyclobutene compound.

21 Claims, 2 Drawing Sheets

PROCESS FOR NITRATING BENZOCYCLOBUTENE COMPOUNDS

DESCRIPTION

1. Technical Field

This invention relates to an improved process for the nitration of benzocyclobutene compounds, which process provides higher yields of nitrobenzocyclobutenes and lower amounts of ring-opening products than known processes.

2. Background Art

Horner et al., *Chem. Ber.*, vol. 93 (1960), pages 1774-1781, carried out nitration of benzocyclobutene with nitric acid in acetic acid at 20°-25° C. The reaction mixture contained 4-nitrobenzocyclobutene (23-28% of theory), dinitro compound and a ring-opening product, identified as beta-(2-nitrophenyl)ethyl nitrate (20% of theory).

Lloyd et al., *Tetrahedron*, vol. 20 (1964), pages 2185-2194, have investigated electrophilic substitution reactions of benzocyclobutene, including nitration. Products of nitration with fuming nitric acid in acetic acid/acetic anhydride included 27% of 4-nitrobenzocyclobutene, less than 5% of 3-nitrobenzocyclobutene, 31% of ortho-(beta-nitroethyl or beta-acetylethyl)nitrobenzene, and about 34% of poly(ortho-nitrostyrene).

Tan et al., U.S. Pat. No. 4,711,964, herein incorporated by reference, obtained 25-35% yields of 4-nitrobenzocyclobutene, after purification by column chromatography, by a similar process. This was reduced, using hydrogen and Pd/Al$_2$O$_3$, to 4-aminbenzocyclobutene. The latter is an important intermediate for the preparation of bisbenzocyclobutene compounds, which can polymerize through an o-xylylene bisdiene moiety.

Cornelis et al., *Chem. Lett.*, (1988), pages 1839-1842, have proposed selective catalytic mononitration of toluene in the presence of modified clays to produce a product mixture, containing large amounts (67%) of p-nitrotoluene.

Cornelis et al., *Tetrahedron Letters*. vol. 29 (1988), pages 5909-5912, have recited selective nitration of aromatic hydrocarbons, e.g., toluene, using lamellar montmorillonite clays, impregnated with metallic nitrates, in the presence of acetic anhydride.

Tanida et al. (U.S. Pat. No. 3,466,330) disclose that nitration of a strained ring aromatic compound with conventional nitrating agents gives mono or dinitro products.

Disclosure of Invention

This invention relates to an improved process for the nitration of a substituted or unsubstituted benzocyclobutene compound in a reaction mixture comprising a nitrating agent, an unhalogenated carboxylic acid anhydride, clay and a solvent to produce a corresponding nitrobenzocyclobutene compound, wherein:

(a) the solvent has a density above that of the nitrating agent or an extractable precursor thereof;

(b) the reaction mixture is heated at a temperature such that solvent is removed from the reaction mixture to a site outside the reaction mixture to extract nitrating agent or extractable precursor thereof; and (c) the thus-extracted nitrating agent or precursor thereof is fed into the reaction mixture to nitrate the benzocyclobutene compound.

This invention further relates to a process for the nitration of a substituted or unsubstituted benzocyclobutene compound, comprising nitrating the benzocyclobutene compound with copper nitrate-loaded clay in a solvent inert to reactants or products in the presence of an unhalogenated carboxylic acid anhydride.

Detailed Description

"Benzocyclobutene," as used in the specification and claims, includes carbocyclic and heterocyclic arylcyclobutene (cyclobutarene) compounds, which consist of a cyclobutene ring fused to an aromatic carbocyclic or heterocyclic ring. Aromatic as used herein refers to carbocyclic or heterocyclic rings in which $4n+2$ delocalized pi electrons are contained in an orbital ring. This property is also known as resonance stabilization or delocalization.

Preferred carbocyclic aromatic moieties include benzene, naphthalene, phenanthrene, anthracene, a biaryl moiety or two or more aromatic radicals, bridged by alkylene or cycloalkylene moieties. More preferred carbocyclic aromatic radicals include benzene, naphthalene, biphenyl, binaphthyl, diphenylalkane or diphenylcycloalkane radicals. The most preferred carbocyclic aromatic radical is a benzene radical, which, when fused to a cyclobutene ring, produces the simplest member of the series, benzocyclobutene.

Examples of preferred heterocyclic aromatic compounds include pyrrole, furan, thiophene, imidazole, oxazole, thiazole, pyrazine, pyridine and pyrimidine. More preferred heterocyclic aromatic radicals are pyridine, furan and thiophene, with cyclobutapyridine being most preferred. The carbocyclic analogs are preferred over the heterocyclic analogs.

Either the aryl radical or the cyclobutene ring can be substituted by electron-donating or electron-withdrawing groups. Examples of such substituents include cyano, halo, carboxy, hydrocarbyloxy, carbonyl, alkanoyl, aroyl, alkylsulfonyl, alkylsulfonoyl, amido, alkyl, alkenyl or aryl groups.

It will be understood that "benzocyclobutene" is an art-recognized term. In the commonly-used non-systematic numbering system for benzocyclobutenes, the 1-and 2-positions are in the cyclobutene ring. The 3- and 6-positions are in an aromatic ring, adjacent to the cyclobutene ring. The 4- and 5-positions are meta- to the cyclobutene ring. The simplest member of the series, benzocyclobutene, is formally identified as bicyclo[4.2.0]octa-1,3,5-triene. A compound, formally identified as 3-nitrobicyclo[4.2.0]octa-1,3,5-triene, is commonly known as 4-nitrobenzocyclobutene. The common names will be used in the specification and claims.

The nitrobenzocyclobutene compounds, obtained by the process of this invention, can be used to make aminobenzocyclobutenes, particularly bridged benzocyclobutenes of the formula

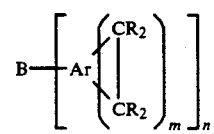

wherein B is an n-valent bridging moiety containing nitrogen, bonded to the aromatic ring (Ar) of the benzocyclobutene unit, m is an integer of 1 or more, n is an integer of 2 or more and each R is hydrogen or an electron-donating or electron-withdrawing substituent.

The nitrobenzocyclobutene products of this invention can also be used to prepare derivatives of unbridged aminobenzocyclobutenes, for example, 4-(N-alkyl or N-alkanoyl)aminobenzocyclobutenes.

In the simplest cases, the cyclobutene ring is unsubstituted (each R is H and m is 1) and the aromatic ring is benzene. This case can be represented by the subgeneric formula

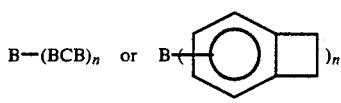

wherein B is the nitrogen-containing bridging function and n is as above. In this formula, BCB represents 4-benzocyclobutenyl.

Examples of nitrogen-containing bridging groups include, but are not limited to,

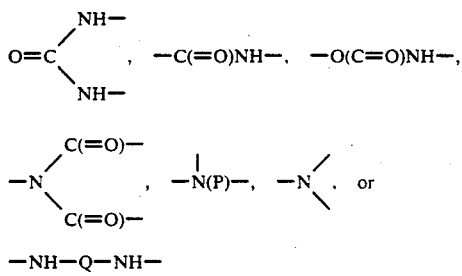

—NH—Q—NH— wherein P is H, alkyl or aryl and Q is a divalent bridging groups, such as phenylene, xylylene, alpha,omega-alkylene and the like. A preferred type of bridging group is that wherein Q is alkylene and the simplest products correspond to the general formula BCB—NH—$C_xH_{2x}$—NH—BCB in which x is an integer from 2-20. Most preferred of these bridging groups include those derived by reaction with 1,4-diaminobutane (tetramethylene diamine) or 1,6-diaminohexane (hexamethylene diamine).

Corresponding oxaalkylene diamines can be used as bridging groups. For example, B can be —NH$C_{x/2}H_x$-O$C_{x/2}H_x$NH—, wherein x is as above. Other nitrogen-containing bridging groups are disclosed by Kirchhoff et al., U.S. Pat. No. 4,540,763, herein incorporated by reference.

More preferred bridging groups include aromatic moieties, such as phenylene, tolylene, xylylene, naphthylenylene and the like, represented by the symbol AR, wherein AR is the residue of an aromatic moiety having n amino groups. The bridged products, containing unsubstituted BCB functionality can therefore be represented by the following typical formulas:

BCB—N(P)—AR—N(P)—BCB,[BCB—N(P)]$_3$AR
and [BCB—N(P)]$_n$AR

That is, AR is the residue of 1,2-diaminobenzene, 1,3-diaminobenzene, 1,4-diaminobenzene, 1,3,5-triaminobenzene, 1,2,4,5-tetraaminobenzene, 1,4,5,8-tetraaminoanaphthalene, 1,5-diaminonaphthalene, 1,4-diaminonaphthalene, diaminoanthracene, triaminoanthracene, diaminophenanthrene, triaminoanthracene and the like.

Exemplary unbridged nitrobenzocyclobutene compounds which can be prepared in accordance with this invention include, but are not limited to, compounds of the structures:

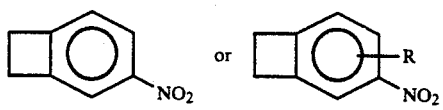

wherein R is alkyl, vinyl, substituted vinyl, ethynyl, substituted ethynyl, aryl, polyaryl, substituted aryl, substituted polyaryl, heterocyclic, heteroaryl, alkylaryl, alkylheterocyclic, arylheteroaryl, trialkylsilyl, nitro, cyanato, formyl, aroyl, alkanoyl, benzobicyclobutenyl, benzocyclobutenoyl, alkylbenzocyclobutenyl, arylbenzocyclobutenyl, alkylarylbenzocyclobutenyl, arylalkylbenzocyclobutenyl, oxybenzocyclobutenyl, thiobenzocyclobutenyl, benzocyclobutenyl sulfonyl, benzocyclobutenyl sulfoxide, carboxy, carbalkoxy, mono or dialkylamino, mono or diarylamino, mono or diheterocyclic amino, mono or diheteroaryl amino, hydroxy, alkoxy, aryloxy, substituted alkoxy, substituted aryloxy, polyaryloxy, substituted polyaryloxy, mercapto, alkylthio, substituted alkylthio, arylthio, substituted arylthio, polyarylthio, substituted polyarylthio, heterocyclothio and heteroarylthio. Substituted compounds include hydrocarbyl substituents, as recited by Kirchhoff, supra.

Representative higher fused ring nitrobenzocyclobutene products include, but are not limited to, compounds of the formulas:

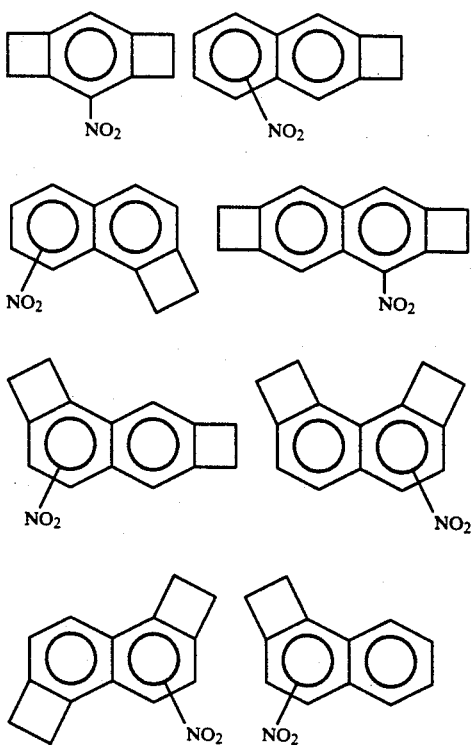

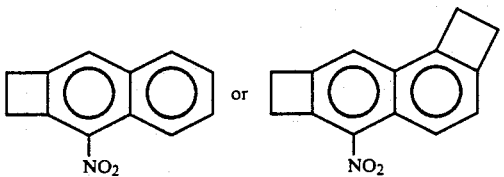

It has been found that the process of this invention is highly selective toward the formation of 4-nitrobenzocyclobutene, rather than of 3-nitrobenzocyclobutene, from benzocyclobutene itself.

It is preferred to use an unhalogenated carboxylic acid anhydride in the practice of this invention. Representative carboxylic acid anhydrides include acetic anhydride, propionic anhydride, butyric anhydride, benzoic anhydride, acetic-benzoic anhydride, toluic anhydride and the like. Acetic anhydride, propionic anhydride and benzoic anhydrides are preferred. Most preferred is acetic anhydride.

Attempted nitration of benzocyclobutene with trifluoracetic anhydride/inorganic nitrate in various solvents gives a mixture of products:

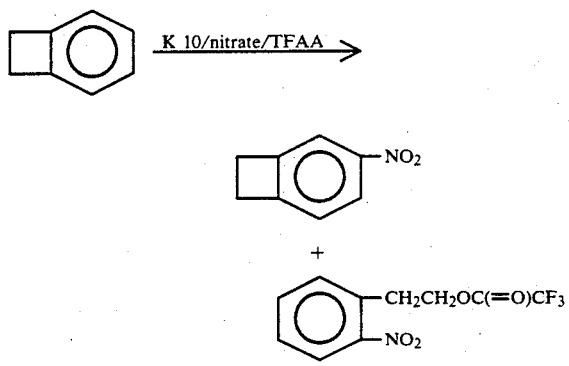

Product mixtures, including the ring-opening product, are also obtained using a variety of other nitrating agents.

The nitrating agent or precursor thereof can be selected from nitric acid of varying strengths, particularly nitric acid above 50% concentration. It will be understood that the active nitrating species may be nitric acid and/or an acyl nitrate, e.g. acetyl nitrate. The active nitrating species is thought to be formed in the reaction mixture, rather than at a site, outside the reaction mixture. However, it has been found that some carboxylic anhydrides, e.g. acetic anhydride, can codistill with the solvent to the source of nitric acid and that formation of acetyl nitrite outside the reaction mixture can not be excluded as a possible source of active nitrating species.

Nitric acid, at concentrations above 50% real, has a density above about 1.31 at 25° C. It is preferred to use more concentrated nitric acid, particularly nitric acid of 60% or higher concentration. The density of 60% nitric acid is about 1.35 at 25° C.

The solvent used in the practice of this invention is selected from solvents which have low boiling points, preferably from about 20° C. to about 100° C., which are inert to the nitrating agent or precursor and the carboxylic acid anhydride and which have a density higher than that of the nitrating agent being used. The solvent is therefore selected from nitroalkanes, such as nitromethane; halocarbons or chlorofluorocarbons. Examples of the latter types of materials include chloroform, methylene chloride, 1,1,2-trichlorotrifluoroethane, benzotrifluoride, trichlorofluoromethane and carbon tetrachloride. A particularly preferred solvent is 1,1,2-trichlorotrifluoroethane, which permits the reaction to be carried out at 40°–60° C.

A preferred process is that, wherein the nitrating agent or precursor is nitric acid of a density above 1.31 at 25° C. and the solvent is of a density above 1.35 at 25° C. More preferably, the solvent is low boiling, is inert to the liquid nitrating agent and carboxylic anhydride and has a density above about 1.40. Most preferably, the solvent boils at from about 40° to about 60° C., is inert to the liquid nitrating agent and carboxylic acid anhydride and has a density above about 1.40.

Liquid halocarbons or chlorofluorocarbons of 1–4 carbon atoms are preferred solvents. A more preferred solvent is a trichlorotrifluoroethane. 1,1,2-Trichlorotrifluoroethane is a most preferred solvent.

It will be understood that mixtures of these solvents can be used.

Clays which can be used in the practice of this invention include various phyllosilicate minerals, which comprise seven different subclasses:

(a) clays having a two-layer structure, including the kaolin group (kaolinite, dickite, nacrite, metahalloysite, halloysite, allophane and anauxite) and the septochlorite group (serpentine, chrysotile, antigorite, picrolite, lizardite, garnierite, percoraite, greenalite, berthierite, bementite, amesite, grovesite and cronstedtite);

(b) clays having primitive three-layered structures, comprising pyrophyllite, talc, minnesotaite and wilemseite;

(c) the micas, including leucophyllite, celadonite, glauconite, phengite, alurgite, mariposite, illite, brammallite, hydromuscovite, muscovite, paragonite, roscoelite, fuchsite, ollacherite, sericite, taeniolite, polylithionite, lepidolite, zinnwaldite, manganophyllite, hendricksite, biotite, phlogopite, siderophyllite, annite and lepidomelane;

(d) brittle micas, including margarite, bityite, ephesite, xanthophillite, clintonite and anandite;

(e) expandable three-layer structures, or pillared clays, including smectites (montmorrillonite, beidellite, nontronite, volchonskoite, hectorite, saponite, stevensite, sauconite and pimelite) and vermiculite;

(f) four-layer structures, including chlorite, thuringite, chamosite, ripidolite, brunsvigite, diabandite, sheridanite, clinochlore, penninite, ferrian, chromian, kammererite, manganian, pennantite, gonyerite, nimite and cookeite; and (g) pseudolayer silicates, including apophophyllite, sanbornite, gillespite, cuprorivaite, palygorskite, sepiolite, prehenite, stipnomelane, fenaksite, chrysocolla, krauskopfite, okenite, nekoite, stillwellite, ekanite, the melilite group (gehlenite, akermanite and hardystonite), leucophanite, meliphanite, datolite, gadoninite, homilite, leucosphenite, dalyite, astrophyllite, kupletskite and niobophyllite.

The clays can be of natural or synthetic origin. Synthetic pillared clays are made, for example, by processes proposed by Shabria et al. (U.S. Pat. No. 4,216,188) or Vaughan et al. (U.S. Pat. No. 4,248,739), both herein incorporated by reference. The state of the art of synthetic layered silicates and aluminosilicates is reviewed by Swift, Chapter 7, "Advanced Materials in Catalysis," Burton et al., eds., Academic Press, New York, 1977, pages 209–233.

Preferably, the clay is a montmorillonite, a pillared clay, a hectorite clay or a synthetic clay. Most preferred is a montmorillonite, identified as K 10 (Aldrich). Another particularly preferred clay is sodium montmorillonite.

The amounts of nitric acid, solvent, carboxylic acid anhydride and clay can be varied from 1.2:25:1.5:0.25 parts by weight to 12:150:15:2.5 parts by weight per part by weight of benzocyclobutene compound. It is preferred to use from about 3:60:2:0.5 to about 4.5:75:25:1 parts by weight, respectively, of nitric acid, solvent, carboxylic acid anhydride and clay per part by weight of benzocyclobutene compound.

A critical aspect of the process of this invention is avoiding direct contact between large quantities or nitric acid or active nitrating species and the benzocyclobutene compound being nitrated, so as to minimize ring opening reactions. One means of accomplishing this is to place a mixture of clay, solvent, carboxylic acid anhydride and benzocyclobutene compound in a flask, fitted out with a reflux condenser and a reverse Dean-Stark trap. Solvent is charged to the reverse Dean-Stark trap to fill most of the volume of the trap and the less dense nitric acid is charged to the trap. This apparatus is shown in FIG. 1. As the reaction mixture is heated, solvent distills out of the flask and is condensed by the reflux condenser, as a result of which the solvent passes through the nitric acid. Any codistilled acid anhydride can also react with the nitric acid to produce an active nitrating species.

In a preferred case, the carboxylic acid anhydride is acetic anhydride and the active nitrating species, thought to be acetyl nitrate, is produced, for the most part, in the reaction mixture.

An alternative method for preventing direct contact between the liquid nitrating agent and the benzocyclobutene compound is by extracting nitric acid, lying in a separate phase above the reaction mixture, with solvent and feeding the thus-extracted nitric acid into the reaction mixture.

Most preferably, the process is that wherein the benzocyclobutene compound is unsubstituted benzocyclobutene.

In another embodiment, a process for the nitration of a substituted or unsubstituted benzocyclobutene compound comprises nitrating a benzocyclobutene compound with copper nitrate-loaded clay in a solvent inert to reactants or products in the presence of an unhalogenated carboxylic acid anhydride. In this process, the preferred solvent is methylene chloride and the preferred carboxylic acid anhydride is acetic anhydride.

The temperature for performing the process of this invention is from about 20° C. to the boiling point of the solvent selected. A temperature below 100° C. is preferred, so as to minimize the competing ring-opening reaction. At the temperatures contemplated, dimerization or oligomerization of benzocyclobutene reactants or products is not a significant side reaction. The upper temperature limit can be determined empirically, by known methods, such as by following the progress of the reaction using gas chromatography.

The time required for nitration of benzocyclobutene compound to nitrobenzocyclobutene compound is a function primarily of the reaction temperature and can be determined empirically, as above. At a representative temperature of 40°–60° C., substantially complete nitration of benzocyclobutene occurs with 18 hours' heating.

The process of this invention can be carried out in any container, with or without a stirring attachment, which can be heated to the required temperature, and which is not attacked by the reactants, catalysts or products of the invention.

Cyclobutapyridines can be prepared by the pyrolysis of 4-pyridyl propargyl ether at 550° C. See J. M. Riemann et al., *Tetrahedron Letters*, no. 22 (1977), pages 1867–1870. Alternatively, a pyridine-4-carbonitrile, having an alkyl substituent on the carbon atom adjacent to the nitrile, is reacted with sodium azide and ammonium chloride in N,N-dimethylformamide to prepare a 5-(alkyl-4-pyridyl)tetrazole. The 5-(alkyl-4-pyridyl)tetrazole is pyrolyzed at about 600° C. to a cyclobutapyridine. See W. D. Crow et al., *Austrailian Journal of Chemistry* (1975), after page 1741.

BEST MODE FOR CARRYING OUT THE INVENTION

In a most preferred process, the carboxylic anhydride is acetic anhydride, the nitric acid is of a density above 1.31 at 25° C., the solvent is 1,1,2-trichlorotrifluoroethane, the clay is montmorillonite K 10, the reaction is carried out in an apparatus including a reflux condenser and a reverse Dean-Stark trap and acetyl nitrate is generated in situ in the reaction mixture.

Without further elaboration it is believed that one skilled in the art can, using the preceding description, utilize the present invention to its fullest extent. The following preferred specific embodiments are, therefore, to be construed as merely illustrative and not limitative of the remainder of the disclosure in any way whatsoever.

In the following examples, the temperatures are set forth uncorrected in degrees Celsius. Unless otherwise indicated, all parts and percentages are by weight.

EXAMPLE 1

Nitration of Benzocyclobutene

Figure 1:
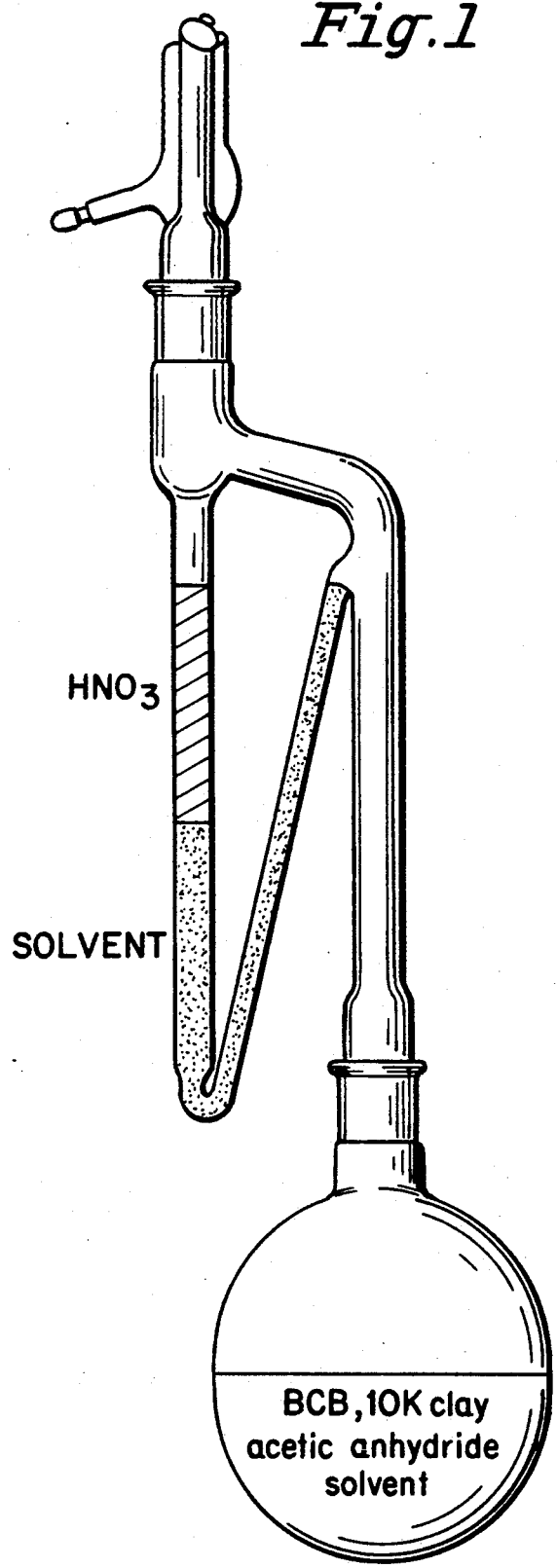
In FIG. 1 is shown an apparatus, suitable for performing a process of this invention.

A mixture of 2 g of benzocyclobutene, 2.5 g of montmorillonite K 10 clay and 5 mL of acetic anhydride in 100 mL of 1,1,2-trichlorotrifluoroethane is placed in a 250-mL round bottom flask, equipped with a magnetic stirrer, reverse Dean-Stark trap, reflux condenser and heating mantle. The apparatus is shown in FIG. 1. Nitric acid (6 g) is charged to the trap as the top layer along with 25 mL of solvent. The reaction mixture is stirred and heated under reflux for 18 h.

During the reaction, the condensed solvent-acetic anhydride mixture passes through the nitric acid before being returned to the flask. Nitric acid is continuously extracted into the system and forms acetyl nitrate in situ.

At the end of the reaction, the mixture is cooled and filtered. The filtrate is washed with water (50 mL), with sodium bicarbonate solution (10%) and saturated sodium chloride solution, after which the organic layer is dried over anhydrous magnesium sulfate. The solvent is removed and the product is purified by flash chromatography in 10% ethyl acetate in hexanes as disclosed by Still et al., *J. Org. Chem.*, vol. 43 (1978), pages 2923-2925.

The yield of 4-nitrobenzocyclobutene is 1.7 g (59.3%).

Figure 2:
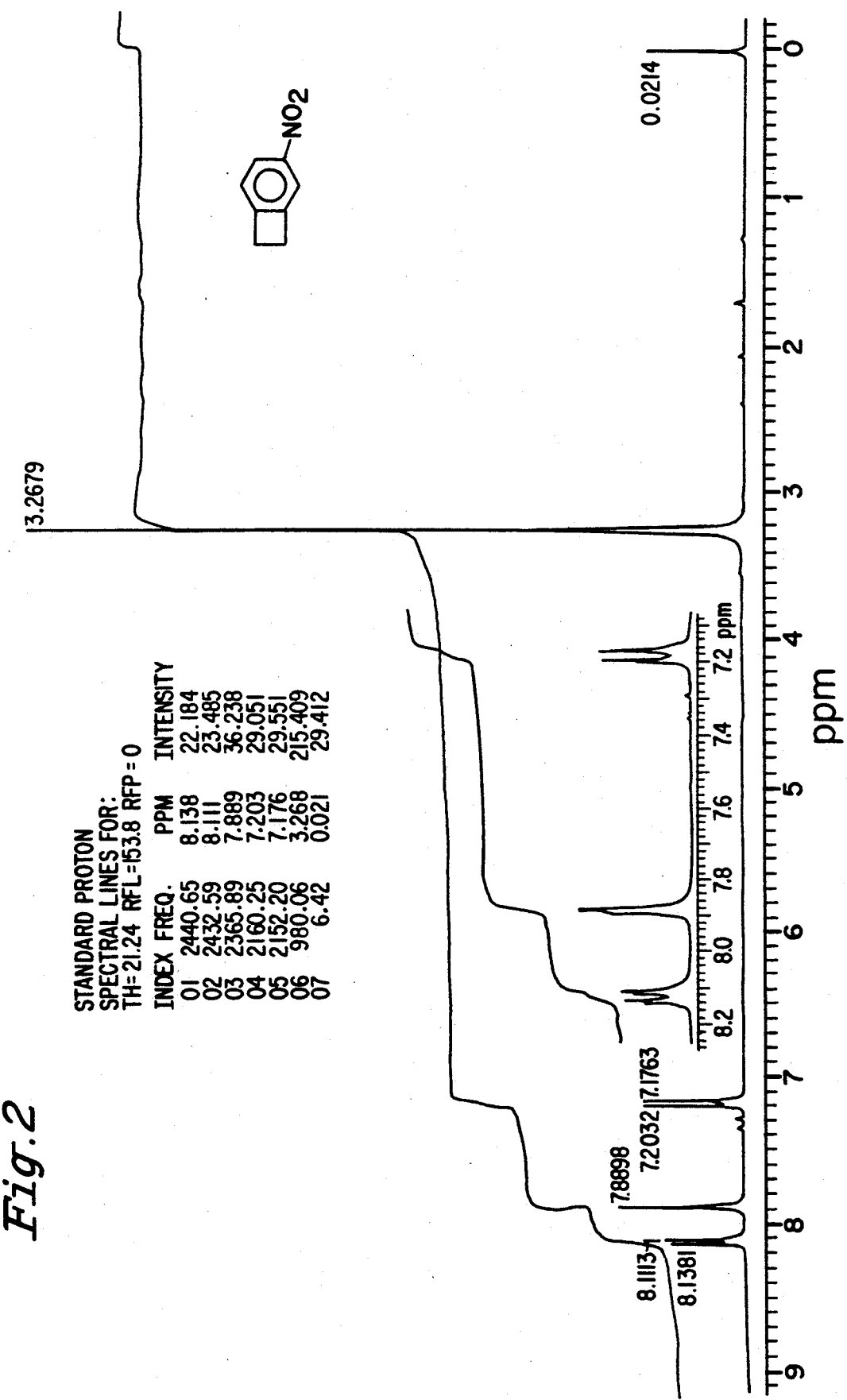
In FIG. 2 is shown the proton NMR spectrum of a product, prepared by the process of this invention.

The proton NMR spectrum of the product is shown in FIG. 2.

EXAMPLE 2

Evaluation of Alternative Nitration Conditions

A variety of reagents for nitrating benzocyclobutene were evaluated. The following results were obtained:

| Reagents/conditions | Results |
|---|---|
| $NO_2BF_4$, sulfolane, 0-10° C. 30 min | 45% $NO_2$-BCB + polymeric materials |
| N-Nitropyridinium tetrafluoroborate (from 2-picoline), acetonitrile, 0° C. to room temperature, 2 days | <5% $NO_2$-BCB + unreacted BCB |
| N-Nitropyridium tetrafluoroborate (from 2,6-lutidine), acetonitrile, 0° C. to room temperature, 2 days | <5% $NO_2$-BCB + unreacted BCB |
| Isopropyl nitrate, $BF_3$, nitromethane, 0° C. to room temperature, 8 h | <5% $NO_2$-BCB + unreacted BCB |
| Isopropyl nitrate, $BF_3$, acetonitrile, 0° to room temperature, 18 h | <5% $NO_2$-BCB + unreacted BCB |
| Isopropyl nitrate, K 10 clay, 1,1,2-trichlorotrifluoroethane, reflux, 12 h | no reaction |
| $NO_2Cl$, $TiCl_4$, nitromethane, 0° C. to room temperature, 1 h | many products |
| Urea nitrate, trifluoroacetic acid, K 10 clay, acetonitrile, 70° C. | no $NO_2$-BCB |
| Nitrourea, K 10 clay, acetonitrile, 82° C. | no $NO_2$-BCB |
| Urea nitrate, acetic anhydride, K 10 clay, 1,1,2-trichlorotrifluoroethane, 20° C. | $NO_2$-BCB:ring-opening product 1:1.7 |
| $N_2O_4$, methylene chloride, 0-15° C. | no reaction |
| $N_2O_4$, $TiCl_4$, methylene chloride, 0-15° C. | no $NO_2$-BCB |

EXAMPLE 3

Evaluation of Representative Clays (a) Experiments are run as in example 1, using various clays. The following results are obtained:

| Clay | Isolated Yield of $NO_2$-BCB |
|---|---|
| Montmorillonite K 10 | 55-60% |
| Na montmorillonite | 61 |
| Dried Na montmorillonite 350° C. for 18 h | 56 |
| Pillared clay | 55 |
| Hectorite | 55 |
| Synthetic clay | 52 |

(b) K 10 montmorillonite clay is impregnated with copper nitrate by the method of Lazlo et al., *J. Org. Chem.*, vol. 52 (1987), pages 2407-2411, using 30 g of clay and 20 g of copper nitrate trihydrate. BCB (2 g) is nitrated with this material (claycop, 5 g) in 50 mL of methylene chloride, containing 5 mL of acetic anhydride at 20° C. for 18 h to give a 46% yield of $NO_2$—BCB. Use of 10 g of claycop and 10 mL of acetic anhydride in a similar reaction gives 59% of 4-$NO_2$BCB.

EXAMPLE 4

Evaluation of Representative Carboxylic Anhydrides

Experiments are run as in Example 1, using various anhydrides. The following results are obtained:

| Anhydride | Isolated Yield of $NO_2$-BCB |
|---|---|
| Acetic | 55-60 |
| Propionic | 55 |
| Benzoic | 54 |

These experiments show that a variety of carboxylic acid anhydrides can be used for the process of the invention.

EXAMPLE 5

Evaluation of Trifluoroacetyl or Trichloroacetyl Nitrates

Trifluoroacetyl nitrate generated in situ from ammonium nitrate (AN) and trifluoroacetic anhydride (TFAA) in methylene chloride is reacted with BCB at 20° C. for 2 h. The product is a 1:1 mixture of $NO_2$—BCB and ring-opening product, 2-(o-nitrophenyl)ethyl acetate.

| Reaction Conditions | $NO_2$-BCB: Ring-opening Product |
|---|---|
| TFAA, AN, methylene chloride, 0° C. | 1:1 |
| TFAA, AN, acetonitrile, 20° C. | 1:2 |
| TFAA, AN, hexane, 20° C. | 1:1 |
| Copper nitrate, methylene chloride, TFAA, 20° C. C. | 1:1.5 |
| Sodium nitrate, methylene chloride, TFAA, 20° C. | 1:1 |
| TFAA, AN, methylene chloride, 0° C., plus K 10 clay | 1:1 |
| Trichloroacetic anhydride, AN, methylene chloride, 20° C. | 1:1 |

These results show that ring opening is a significant side reaction when a trihaloanhydride/nitrate mixture is used to produce the nitrating agent.

EXAMPLE 6

Nitration of BCB by Direct Introduction of Nitric Acid into the Mixture

Nitric acid (d=1.4, 2.52 g) is introduced slowly over 2 h into a suspension of BCB, K 10 clay, 1,1,1-trichlorotrifluoroethane and acetic anhydride, otherwise treated as in Example 1. The product is a 1:1 mixture of 4-nitrobenzocyclobutene and 2-(o-nitrophenyl)ethyl acetate.

EXAMPLE 7

Variation of Solvent

Reactions are run as in Example 1, using as solvent methylene chloride, chloroform or benzotrifluoride. Similar results are obtained.

EXAMPLE 8

Nitric acid is extracted from nitric acid, lying in a separate phase above a reaction mixture containing benzocyclobutene, acetic anhydride, 1,1,2-trichlorotrifluoroethane, and montmorillonite clay. The extracted nitric acid passes from the nitric acid layer to the reaction mixture to form acetyl nitrate, which is a reactive nitrating agent, or to nitrate the benzocyclobutene directly.

EXAMPLE 9

A mixture of acetic anhydride and 1,1,2-trichlorotrifluoroethane are placed in a round-bottom flask, equipped with a reverse Dean-Stark trap and reflux condenser. After the mixture is heated under reflux, solvent is collected from the trap. GC analysis of collected solvent shows the presence of acetic anhydride.

This experiments shows that acetic anhydride can distill from the reaction mixtures with the solvent and that acetyl nitrate can be formed in the reverse Dean-Stark trap and fed into a reaction mixture.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

We claim:

1. A process for the nitration of a substituted or unsubstituted benzocyclobutene compound in a reaction mixture comprising a nitrating agent, an unhalogenated carboxylic acid anhydride, clay and a solvent to produce a corresponding nitrobenzocyclobutene compound, wherein:
   (a) the solvent has a density above that of the nitrating agent or an extractable precursor thereof;
   (b) the reaction mixture is heated at a temperature such that solvent is removed from the reaction mixture to a site outside the reaction mixture to extract nitrating agent or extractable precursor thereof; and
   (c) the thus-extracted nitrating agent or precursor thereof is fed into the reaction mixture to nitrate the benzocyclobutene compound.

2. The process of claim 1, wherein the carboxylic acid anhydride is acetic anhydride.

3. The process of claim 1, wherein the carboxylic acid anhydride is propionic anhydride.

4. The process of claim 1, wherein the carboxylic acid anhydride is benzoic anhydride.

5. The process of claim 1, wherein the nitrating agent or precursor thereof is nitric acid of a density above 1.31 at 25° C. and the solvent is of a density above 1.35 at 25° C.

6. The process of claim 1, wherein the solvent is low boiling, is inert to the nitrating agent and carboxylic anhydride, has a density above about 1.40 and is selected from nitromethane, chloroform, methylene chloride, trichlorotrifluoroethane, benzotrifluoride, trichlorofluoromethane and carbon tetrachloride.

7. The process of claim 1, wherein the solvent boils at from about 40° to about 60° C., is inert to the nitrating agent and carboxylic acid anhydride and has a density above about 1.40.

8. The process of claim 6, wherein the solvent is a liquid halocarbon or chlorofluorocarbon selected from chloroform, methylene chloride, trichlorotrifluoroethane, trichlorofluoromethane and carbon tetrachloride.

9. The process of claim 8, wherein the solvent is a trichlorotrifluoroethane.

10. The process of claim 9, wherein the solvent is 1,1,2-trichlorotrifluoroethane.

11. The process of claim 1, wherein the clay is a montmorillonite, a pillared clay, a hectorite clay or a synthetic clay.

12. The process of claim 1, wherein the clay is a montmorillonite.

13. The process of claim 1, wherein the clay is montmorillonite K 10 clay.

14. The process of claim 1, wherein the clay is sodium montmorillonite.

15. The process of claim 1, carried out in an apparatus including a reflux condenser and a reverse Dean-Stark trap.

16. The process of claim 15, wherein the carboxylic acid anhydride is acetic anhydride and acetyl nitrate is generated in situ in the reaction mixture.

17. The process of claim 1, wherein nitric acid, lying in a separate phase above the solvent, is extracted by the solvent and fed into the reaction mixture.

18. The process of claim 1, wherein the benzocyclobutene compound is unsubstituted benzocyclobutene.

19. The process of claim 1, wherein the carboxylic anhydride is acetic anhydride, the nitrating agent or precursor is thereof nitric acid of a density above 1.31 at 25° C., the solvent is 1,1,2-trichlorotrifluoroethane, the clay is montmorillonite K 10, the reaction is carried out in an apparatus including a reflux condenser and a reverse Dean-Stark trap and acetyl nitrate is generated in situ in the reaction mixture.

20. A process for the nitration of a substituted or unsubstituted benzocyclobutene compound, comprising nitrating the benzocyclobutene compound with copper nitrate-loaded clay in a solvent inert to reactants or products in the presence of an unhalogenated carboxylic acid anhydride.

21. The process of claim 20, wherein the solvent is methylene chloride and the anhydride is acetic anhydride.

* * * * *